April 18, 1972 J. W. PATTERSON Plant Pat. 3,113
ROSE PLANT
Filed Feb. 2, 1970
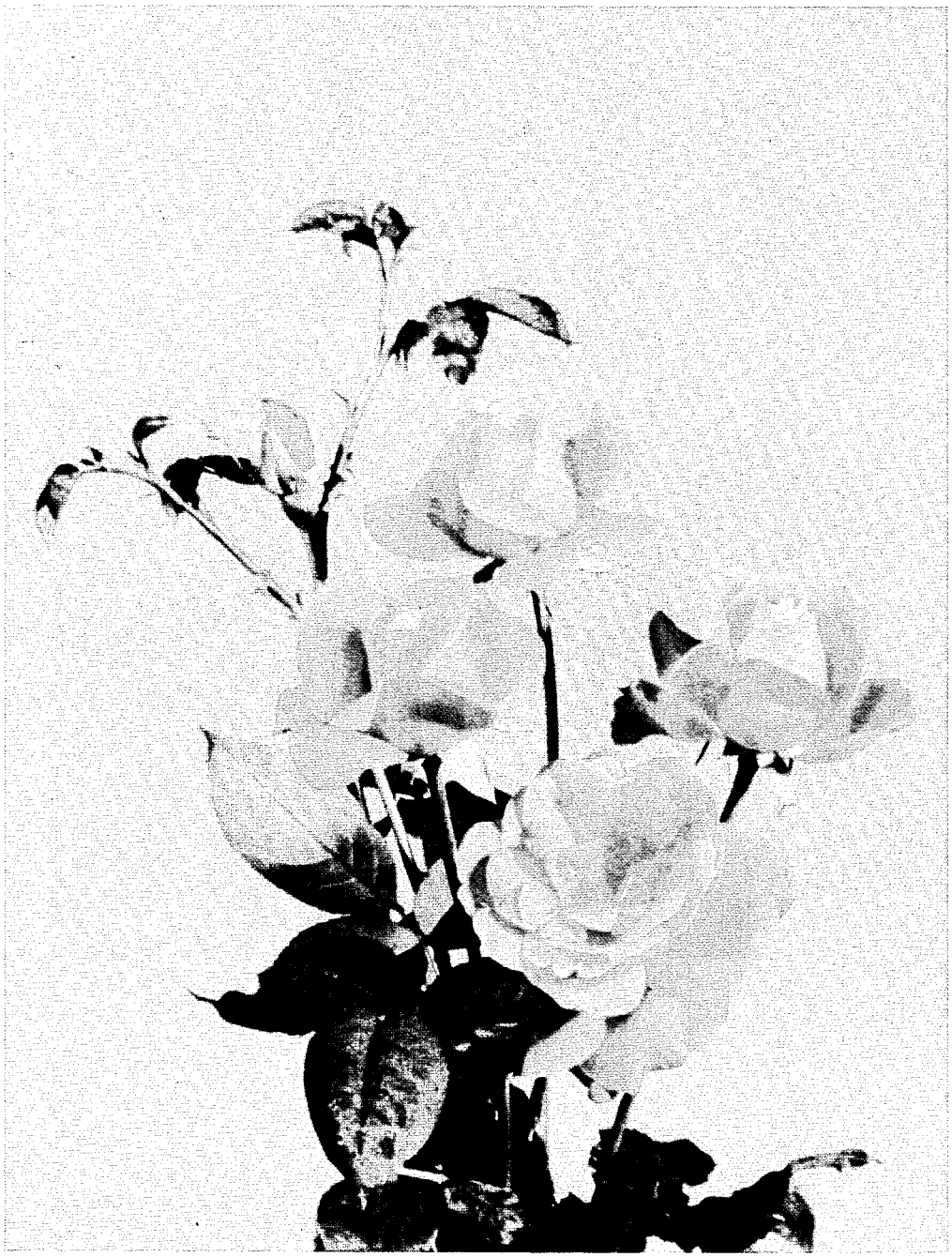

United States Patent Office

Plant Pat. 3,113
Patented Apr. 18, 1972

3,113
ROSE PLANT

John W. Patterson, Houston, Tex., assignor to Patterson Roses, Houston, Tex.

Filed Feb. 2, 1970, Ser. No. 8,100
Int. Cl. A01h *5/00*
U.S. Cl. Plt.—19 1 Claim The present invention relates to a new and distinct variety of rose plant of the grandiflora class, which was originated by me by crossing the variety "Queen Elizabeth" (Plant Patent No. 1,259) with the variety "Happiness" (Plant Patent No. 911).

The primary objective in making this cross was to produce a new variety of rose plant which combines the most desirable characteristics of the two parent varieties and at the same time produce a different and distinct variety. The object was achieved, as seen by the fact that my new variety is characterized by an unusual color progression of its blooms which at first are deep pink, later showing goldtones in center of bloom at base of petals. My new variety is characterized by its many-flowered cluster habit of its blooms at times and by the height of plant as inherited from the parent "Queen Elizabeth."

In comparison with its seed parent, "Queen Elizabeth," my new variety is definitely distinguished from its parent by the color of the blooms.

As compared with its pollen parent "Happiness," my new variety is distinct therefrom as shown by the color of blooms, more continuous blooming habit and type of plant.

Asexual reproduction of my new variety of budding as performed at Houston, Tex., Wills Point, Tex., and Tyler, Tex., shows that the foregoing characteristics and distinctions of my new variety come true to form and are established and transmitted through succeeding propagations.

The accompanying drawing shows typical specimens of the blooms and foliage of my new variety in different stages of development, as depicted in color as nearly true as it is reasonably possible to make the same in a color illustration of this character.

The following is a detailed description of my new variety, with color terminology in accordance with the Horticultural Colour Chart of the Royal Horticultural Society:

Type: Bush; outdoor; seedling for garden decoration.
Class: Grandiflora.
Breeding: Seedling.
*Seed parent.*—"Queen Elizabeth."
*Pollen parent.*—"Happiness."
Propagation: Holds its distinguishing characteristics through succeeding propagation by budding.

*Flower*

Locality where grown and observed: Houston, Tex., also Wills Point and Tyler, Tex.
Flowers borne: Usually several to stem, sometimes only one to stem.
Quantity of bloom: Free to abundant, outdoors.
Continuity: Continuous during growing season.
Fragrance: Moderate.
Bud:
*Peduncle.*—Long length; smooth; no prickles.
*Color.*—Scheeles Green, Plate 860/1, page 175.
*Before calyx breaks.* — Size — medium to large. Form—long and pointed.
*As calyx breaks.*—Color—Currant Red, Plate 821, page 167, with tip of base Yellow Ochre, Plate 07/1, page 101.

*Sepals.*—Inner surface — Color — Scheeles Green, Plate 860/3, page 175, overlaid with white woolly tomentum; outside surface—Lettuce Green, Plate 861/1, page 176.
*As first petal open.*—Size—medium to large. Form—medium length; wide, ovoid shaped. Color—outside—Currant Red, Plate 821/2, page 167; inside—Currant Red, Plate 821/3, page 167.
*Opening.*—Opens slowly but well; is not retarded by hot, cold, dry or wet weather.
Bloom:
*Size when fully open.*—5 inches:
*Petalage.*—Very double; about 40 to 50 petals. Some blooms have a few petaloids.
*Form.*—High centered at first; opens almost flat, slightly cupped.
Petals:
*Texture.*—Good substance, slightly velvety.
*Shape.*—Broadly obovate, with most slightly repand.

This description of a newly opened flower was made from a rose grown outdoors in the month of October, at Houston, Tex.

*Color.*—*Outside petal*—Outside surface—Spinel Red, Plate 0023, page 189 to near Currant Red, Plate 821/3, page 167; inside surface—Spinel Red, Plate 0023, page 189. Base of petals Yellow Ochre, Plate 07/1, page 101. *Intermediate petal*—outside surface—near Spinel Red 0023/1, page 189; inside surface—Spinel Red, Plate 0023/1, page 189. *Inner petal*—outside and inside surface—near Spinel Red, Plate 0023/1, page 189.

This description was made from a rose that was open for three days outdoors in the month of October, at Houston, Tex.

*Color.*—*Outside petal*—outside surface and inside surface Spinel Red, Plate 0023, page 189. *Intermediate petal*—outside surface—near Currant Red, Plate 821/3, page 167; inside surface—Spinel Red, Plate 0023, page 189. *Inner petal*—both outside and inside surface—Spinel Red 0023, page 189. Small amount of Yellow Ochre, Plate 07/1, page 101, glows at base of inner petals.
*General color effect.*—Newly opened flower—Spinel Red, Plate 0023, page 189. Three days open flower—Spinel Red, Plate 0023, page 189, to Spinel Red, Plate 0023/1, page 189.
*Behavior.*—Drops off cleanly, odor slightly enhanced by cooler weather.
*Flower longevity.*—On bush in garden—5 to 6 days in October. Cut flowers grown outdoors and kept at living room temperature—about 6 days in October.

*Reproductive organs*

Stamens: Many, arranged regularly around pistils.
Filaments: Some short and some long length. Color—Saffron Yellow, Plate 7/3, page 7.
Anthers: Medium large; all open approximately at once. Color—Yellow Ochre, Plate 7/1, page 101.
Pollen: Much. Color—Saffron Yellow, Plate 7/2, page 7.
Pistils: Average amount.
Styles: Uneven; bunched, medium length. Color—Aureolin, Plate 3/2, page 3.
Stigma: Color—Lemon Yellow, Plate 4/1, page 4.
Hips: Many (if old blooms allowed to remain on plant); smooth, round.
Seeds: 15 to 20 per hip.

*Plant*

Foliage:
*Leaves.*—Compound of usually 5 to 7 leaflets; normal; soft, medium to large size.

*Leaflets.*—Shape—ovate; apex—acute; base—round; margin—serrate.

*Color.*—Mature — upper surface — near Spinach Green, Plate 0960/1, page 187; under surface—near Scheeles Green, Plate 860, page 175, overlaid with Ruby Red, Plate 827/2, page 171. Young—upper surface—Spinach Green, Plate 0960/2, page 187, slightly overlaid with Pansy Purple, Plate 928/3, page 177; under surface—Spinach Green, Plate 0960/3, page 187, heavily overlaid with Pansy Purple, Plate 928/3, page 177.

*Rachis (the supporting stem of the compound leaf).*—Average size; upper side—grooved; under side—smooth.

*Stipules.*—Medium to long length; with points turning out at less than 45° angle.

*Disease resistance.*—Very resistant to mildew and blackspot, compared with other varieties grown comparable cultural conditions at Houston and Tyler, Tex.

Growth:

*Habit.*—Bush; upright; tall; compact.

*Growth.*—Hardy; vigorous.

*Canes.*—Medium.

*Main stems.*—Color—Spinach Green, Plate 0960/1, page 187. Straight, good length. *Thorns*—few, medium length, color—slightly lighter than Garnet Brown, Plate 00918/3, page 192. *Prickles and hairs*—none.

*Branches.*—Color—Spinach Green, Plate 0960/3, page 187. *Thorns*—few; color—near Garnet Brown, Plate 00918/3, page 192. Straight sharp points. *Prickles and hairs*—none.

*New shoots.*—Color—Scheeles Green, Plate 860/3, page 175, overlaid with Pansy Purple, Plate 928/3, page 177. *Prickles*—few; color—near Pansy Purple, Plate 928/3, page 177.

I claim:

1. A new and distinct variety of rose of the grandiflora class, substantially as herein shown and described characterized particularly as to the unique combination of good growing and flower producing habits, soft green foliage, relatively large beautiful flowers, of good form at all stages of bloom, moderate fragrance, better than average disease resistance, good, vigorous upright bush, a distinctive and attractive color tonality of the flowers, corresponding to Spinel Red, Plate 0023, page 189, in newly opened flowers and Spinel Red, Plate 0023 to Spinel Red, Plate 0023/1, page 189 in three days open flowers, with a small amount of Yellow Ochre, Plate 07/1, at the bases of petals in the center of the flower glowing throughout, to classify the variety as a blend.

No references cited.

ROBERT E. BAGWILL, Primary Examiner